(12) United States Patent
Boots

(10) Patent No.: US 8,431,531 B2
(45) Date of Patent: *Apr. 30, 2013

(54) METHODS FOR STIMULATING GLUCAGON-LIKE PEPTIDE-1(GLP-1) SECRETION AND TREATMENTS COMPRISING SAME

(75) Inventor: Jan-Willem Pieter Boots, Bilthoven (NL)

(73) Assignee: Campina Nederland Holding B.V., Zaltbommel (NL)

( * ) Notice: Subject to any disclaimer, the term of this patent is extended or adjusted under 35 U.S.C. 154(b) by 330 days.

This patent is subject to a terminal disclaimer.

(21) Appl. No.: 12/095,346

(22) PCT Filed: Nov. 30, 2006

(86) PCT No.: PCT/NL2006/050301
§ 371 (c)(1),
(2), (4) Date: Sep. 8, 2008

(87) PCT Pub. No.: WO2007/064208
PCT Pub. Date: Jun. 7, 2007

(65) Prior Publication Data
US 2009/0036351 A1 Feb. 5, 2009

(30) Foreign Application Priority Data
Nov. 30, 2005 (EP) .................................. 05111521

(51) Int. Cl.
*A61K 38/00* (2006.01)
*A61K 38/08* (2006.01)

(52) U.S. Cl.
USPC ............ 514/4.8; 514/5.7; 514/6.9; 514/16.6; 514/17.9; 514/21.7

(58) Field of Classification Search .................. None
See application file for complete search history.

(56) References Cited

U.S. PATENT DOCUMENTS

| | | | |
|---|---|---|---|
| 5,405,637 A * | 4/1995 | Martinez et al. .............. | 426/580 |
| 5,681,586 A | 10/1997 | Gordon | |
| 7,053,055 B2 | 5/2006 | Demuth et al. | |
| 2002/0182301 A1 | 12/2002 | Draaisma et al. | |
| 2004/0151738 A1 | 8/2004 | Oriol et al. | |
| 2004/0152745 A1 | 8/2004 | Jackson et al. | |
| 2004/0259919 A1 | 12/2004 | Magnin et al. | |
| 2008/0221023 A1 | 9/2008 | Boots | |

FOREIGN PATENT DOCUMENTS

| | | |
|---|---|---|
| DE | 42 11 878 A1 | 10/1993 |
| EP | 1201137 A1 | 5/2002 |
| EP | 1367065 A1 | 12/2003 |
| EP | 1 422 293 A1 | 5/2004 |
| JP | 04-264098 A | 9/1992 |
| JP | 08-099994 A | 4/1996 |
| JP | 2002-284668 A | 10/2002 |
| WO | WO-95/11689 | 5/1995 |
| WO | WO-98/02165 A1 | 1/1998 |
| WO | WO-00/54603 A1 | 9/2000 |
| WO | WO-00/77031 A2 | 12/2000 |
| WO | WO 01/37850 A2 | 5/2001 |
| WO | WO-02/13850 A1 | 2/2002 |
| WO | WO-02/45523 A2 | 6/2002 |
| WO | WO-02/094038 A1 | 11/2002 |
| WO | WO-03/002593 A2 | 1/2003 |
| WO | WO-03/035051 A2 | 5/2003 |
| WO | WO-03/074129 A1 | 9/2003 |
| WO | WO-03/102195 A1 | 12/2003 |
| WO | WO-03/105882 A1 | 12/2003 |
| WO | WO 2004/002241 A1 | 1/2004 |
| WO | WO 2004/022083 A1 | 3/2004 |
| WO | WO-2004/024177 A1 | 3/2004 |
| WO | WO-2004/069265 A1 | 8/2004 |
| WO | WO-2004/098644 A1 | 11/2004 |
| WO | WO-2005/081628 A2 | 9/2005 |
| WO | WO 2005/081628 A2 | 9/2005 |
| WO | WO 2005/117933 A1 | 12/2005 |
| WO | WO-2006/005757 A2 | 1/2006 |
| WO | WO 2006/068480 A2 | 6/2006 |
| WO | WO-2006/068480 A3 | 6/2006 |

OTHER PUBLICATIONS

Cordier-Bussat Martine et al: "Peptones stimulate both the secretion of the incretin hormone glucagon-like peptide 1 and the transcription of the proglucagon gene" Diabetes, vol. 47, No. 7, Jul. 1998.
Cuber J.C. et al: "Luminal CCK-Releasing Factors in the Isolated Vasculary Perfused Rat Duodenojejunum" American Journal of Physiology, vol. 259, No. 2 Part 1, 1990.
Aoyama T et al, "Effect of Soy and Milk Whey Protein Isolates and Their Hydrolysates on Weight Reduction in Genetically Obese Mice" Bioscience Biotechnology Biochemistry, Japan Soc. for Bioscience, Biotechnology and Agrochem, Tokyo, JP, vol. 64, No. 12, Dec. 2000.
Robert Marie-Claude et al: "Identification of Angiotensin-I-Converting Enzyme Inhibitory Peptides derived from sodium caseinate Hydrolysates produced by *Lactobacillus helveticus* NCC 2765" Journal of Agricultural and Food Chemistry, vol. 52, No. 23, Nov. 17, 2004.
Perpetuo, E. A., et al: "Biochemical and pharmacological aspects of two bradykinin-potentiating peptides obtained from tryptic hydrolysis of casein" Journal of Protein Chemistry, vol. 22, No. 7-8, Nov. 2003.
International Search Report mailed Oct. 26, 2006 in International Application No. PCT/NL2005/050056, 7 pages.
Ahren, B et al., "Inhibition of dipeptidyl peptidase IV improves metabolic control over a 4-week study preriod in type 2 diabetes" Diabetes Care, vol. 25, pp. 869-875, 2002.

(Continued)

*Primary Examiner* — Robert Landsman
*Assistant Examiner* — Ian Dang
(74) *Attorney, Agent, or Firm* — Gilberto M. Villacorta; Sunit Talapatra; Foley & Lardner LLP

(57) ABSTRACT

A protein hydrolysate having a degree of hydrolysis between 1 and 40% and containing between 1 and 70 wt. % of peptides having a molecular weight of less than 500 Da and less than 55 wt. % of peptides or proteins having a molecular weight of more than 5000 Da, on the basis of the total proteinaceous material of the composition, is effective in stimulating secretion of glucagon-like peptide-1 (GLP-1). In addition, the hydrolysate may have DPP-IV inhibiting activity. The hydrolysate is suitable for the manufacture of a medicament, or food product for prophylaxis and/or treatment of a GLP-1 mediated condition, in particular obesity, type 2 diabetes mellitus and an immunological disorder.

13 Claims, 2 Drawing Sheets

OTHER PUBLICATIONS

Aoyama T et al., "Effect of Soy and Milk Whey Protein Isolates and their Hydrolysates on Weight reduction in Genetically Obese Mice" Bioscience Biotechnology Biochemistry, vol. 64, No. 12, Dec. 2000, pp. 2594-2600.

Conarello, SL et al., "Mice lacking dipeptidyl peptidase IV are protected against obesity and insulin resistance" Proc. Nat. Acad. Sci. USA, vol. 100, pp. 6825-6830, 2003.

Cordier-Bussat M et al., "Peptones Stimulate Both the Secretion of the Incretin Hormone Glucagon-Like Peptide 1 and the Transcription of the Proglucagon Gene," Diabetes, vol. 47, No. 7, Jul. 1998, pp. 1038-1045.

Cuber J.C. et al., "Luminal CCK-Releasing Factors in the Isolated Vascularly Perfused Rat Duodenojejunum," American Journal of Physiology, vol. 259, No. 2, Part 1, 1990, pp. G191-G197.

Database WPI, Section Ch, Week 199245 Derwent Publications Ltd., London, GB, AN 1992-368170, JP 04-264098 A, Sep. 18, 1992 [XP002402537].

Database WPI, Section Ch, Week 200316 Derwent Publications Ltd., London, GB, AN 2003160072, JP 2002-284668 A, Oct. 3, 2002 [XP002402536].

Database WPI, Week 199625 Derwent Publications Ltd., London, GB, AN 1996-246958, JP 08-099994 A, Apr. 16, 1996 [XP002402538].

Davy et al., "Purification and characterization of barley dipeptidyl peptidase IV" Plant Physiol., vol. 122, pp. 425-432, 2000.

Deacon, CF et al., "Dipeptidyl peptidase IV inhibition potentiates the insulintropic effect of glucagon-like peptide 1 in the anesthetized pig" Diabetes, vol. 47, pp. 764-769, 1998.

Hernandez-Ledesma Blanca et al, "Angiotensin converting enzyme inhibitory activity in commercial fermented products. Formation of peptides under simulated gastrointestinal digestion," Journal of Agricultural and Food Chemistry, vol. 52, No. 6, Mar. 24, 2004, pp. 1504-1510.

Lange et al., "Global expression profiling and physiological characterization of *Corynebacterium glutamicum* grown in the presence of L-valine," Applied and Environmental Microbiology, vol. 69, No. 5, May 2003, pp. 2521-2532 [XP002401827].

Lemieux et al., "Application of Reversed-Phase High-Performance Liquid Chromatography to the Separation of Peptides from Phosphorylated Anddephosphorylated Casein Hydrolysates," Science Publishers B.V., Amsterdam, NL, vol. 473, No. 1, 1989, pp. 189-206 [XP 009070046].

Lemieux et al., "High Performance Liquid Chromatography of Casein Hydrolysates Phosphorylated and Dephosphorylated," Jounal of Chromatography, Science Publishers B.V., Amsterdam, NL, vol. 519, No. 2, Nov. 2, 1990, pp. 299-321 [XP 009070060].

Lemieux et al., "Separation of a Casein Hydrolyzate by HPSEC with a New Mobile Phase and Characterization of Peptides by FABMS," Analytica Chimica Acta, Amsterdam, NL, vol. 352, No. 1-3, Oct. 10, 1997, pp. 399-409 [XP 009070061].

Marie Claude, R. et al., "Identification of Angiotensin-I-Converting Enzyme Inhibitory Peptides Derived from Sodium Caseinate Hydrolysates Produced by *Lactobacillus hleveticus* NCC 2765," Journal of Agricultural and Food Chemistry, vol. 52, No. 23, Nov. 17, 2004, pp. 6923-6931.

Meneilly, GS et al., "Effects if 3 Months of Continuous Subcutaneous Administration of Glucagon-like Peptide 1 in Edlerly Patients with Type 2 Diabetes" Diabetes Care, vol. 26, pp. 2835-2841.

Naslund, E. et al., "Glucagon-like peptide 1 increases the perdio of postprandial satiety and slows gastric emptying in obese men" Am.J. Clin.Nutr., vol. 68, pp. 525-530, 1998.

Perpetuo, E.A, et al. Biochemical and Pharmacological Aspects of Two Bradykinin-Potentiating Peptides Obtained from Tryptic Hydrolysis of Casein, Journal of Protein Chemistry, vol. 22, Nos. 7/8, Nov. 2003, pp. 601-606.

Reinhold, D et al., "Dipeptidyl peptidase IV (CD26)L Role in t cell activation and autoimmune disease" Cellular Peptidases in Immune Functions and Diseases 2, Langner and Ansorge ed., Kluwer Academics/Plenum Publishers, pp. 155-160, 2000.

Steinbrecher, A. et al., "Dipeptidyl Peptidase IV in inflammatory CNS disease" Cellular Peptidases in Immune Functions and Diseases 2, Langner and Ansorge ef., Kluwer Academics/Plenum Publishers, pp. 145-153, 2000.

Tanaka S et al., "Suppression of Arthritisby the inhibitors of dipeptidyl peptidase IV" Int. J. Immunopharmac., vol. 19, pp. 15-24, 1997.

Van Der Ven Cornelly et al., "Reversed phase and size exclusion chromatography of milk-protein hydrolysates: Relation between elution from reversed phase column and apparent molecular weight distribution," International Dairy Journal, vol. 11, No. 1-2, 2001, pp. 83-92 [XP002401826].

Van Elswijk et al., "Rapid detection and identification of angiotensin-converting enzyme inhibitors by on-line liquid chromatography-biochemical detection, coupled to electroscopy mass spectrometry" J. Chromatography, vol. 1020, pp. 45-58, 2003.

Van Loon et al., "Plasma insulin responses after ingestion of different amino acid or protein mixtures with carbohydrate," 2000, Journal of American Society for Clinical Nutrition, Issue 72, pp. 96-105.

\* cited by examiner

```
                        SEQUENCE LISTING

<160> NUMBER OF SEQ ID NOS: 20

<210> SEQ ID NO 1
<211> LENGTH: 30
<212> TYPE: PRT
<213> ORGANISM: Unknown
<220> FEATURE:
<223> OTHER INFORMATION: Description of Unknown: Glucagon-like peptide 1
      sequence

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Leu Pro Leu Pro
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

His Pro Ile Lys
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 4

Leu Pro Val Pro
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Met Pro Leu Trp
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Pro Phe Pro
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Pro Leu Leu Gln
1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Val Leu Pro
1

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Pro Phe Pro Glu
1               5

<210> SEQ ID NO 10
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 10

Leu Pro Gln Tyr Leu
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Pro Val Pro Gln
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Pro Tyr Pro Gln
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Pro Phe Pro Glu Val Phe
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Pro Phe Pro Ile Ile Val
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Met Pro Phe Pro Lys
1               5
```

```
<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Gln Ser Val Leu Ser
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Tyr Val Pro Glu Pro Phe
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Val Pro Leu Gly Thr Gln
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Pro Val Pro Gln Lys
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Val Thr Lys Cys Cys Thr Glu
1               5
```

METHODS FOR STIMULATING GLUCAGON-LIKE PEPTIDE-1(GLP-1) SECRETION AND TREATMENTS COMPRISING SAME

SEQUENCE LISTING

The instant application contains a Sequence Listing which has been submitted via EFS-Web and is hereby incorporated by reference in its entirety. The Sequence Listing (ASCII copy), created on Aug. 19, 2010, is named 69818625.txt and is 4,461 bytes in size.

The present invention relates to methods and means of providing glucose homeostasis, mitigating diabetes effects, inducing satiety and controlling obesity, through stimulation of cellular release of glucagon-like peptide 1 (GLP-1). The invention also pertains to peptides to be used in such methods and means, as well as to nutritional and pharmaceutical products containing these peptides.

BACKGROUND

GLP-1 is an incretin hormone that is released postprandially. GLP-1 has multi-faceted actions, including glucose-induced stimulation of insulin biosynthesis and secretion, inhibition of glucagon secretion, regulation of gene expression, trophic effects on 13 cells, inhibition of food intake, and slowing of gastric emptying. These effects contribute to the normalisation of elevated blood glucose, as well as to the control of satiety and body weight. GLP-1 has been shown to reduce postprandial and fasting glycaemia in subjects with type 2 diabetes mellitus and may therefore be a potentially useful new therapeutic agent in the treatment of type 2 diabetes mellitus. Moreover, GLP-1 could be used to increase satiety and also to prevent and treat obesity.

GLP-1 is related in sequence to GLP-2, glucagon, GIP (Gastric Inhibitory Polypeptide or Glucose-dependent Insulinotropic Polypeptide) and other members of the glucagon peptide superfamily. Many of these peptides exhibit an alanine at position 2, rendering them substrates for degradation by the enzyme dipeptidyl peptidase IV (DPP-IV). Indeed, GLP-1 is rapidly degraded in plasma and therefore has a very short half-life of about 1-2 min. DPP-IV is a multifunctional transmembrane glycoprotein that contains N-terminal dipeptidase activity, which is present on most mammalian cells, in a variety of tissues such as liver, kidney, small intestine, salivary gland, blood cells and plasma. Inhibition of DPP-IV will result in prolongation of the circulating half-life of GLP-1, such that GLP-1 levels increase as to be able to act as a therapeutic agent.

WO 01/37850 describes the stimulating effect of casein glycomacropeptide (CGMP) obtained by rennet hydrolysis of milk (single cleavage of K-casein) on the GLP-1 release in an intestinal cell line. EP 1367065 discloses the use of acid-soluble proteins from micellar casein for increasing GLP-1 or GLP-2 secretion.

WO2004/002241 describes the use of undefined whey proteins and whey protein hydrolysates, in particular α-lactalbumin and β-lactoglobulin hydrolysates, capable of inducing cellular release of GLP and CKK.

Proteins, in particular milk proteins, are commonly known as precursors of a range of biologically active peptides. The fact that proteins are precursors of biologically active molecules is particularly attractive for the development of functional foods, such as foods that may aid in any of the above GLP-1 mediated conditions. Food protein hydrolysates are well-used food ingredients and are of natural origin, such that no synthetic ingredients are required for obtaining the functional effect, in casu stimulation of secretion of GLP-1 and inhibition of its degradation so as to prevent or treat GLP-1 mediated conditions such as obesity, type 2 diabetes mellitus and immunological disorders.

Thus, it is desired to provide protein hydrolysates that are enriched in peptides that stimulate the secretion GLP-1 and optionally inhibit DPP-IV activity, such that they may aid in prevention and treatment of the above-identified GLP-1 mediated conditions. It was found that protein hydrolysates, such as e.g. milk protein hydrolysates could be used for stimulating GLP-1.

DESCRIPTION OF THE INVENTION

Figure 1:
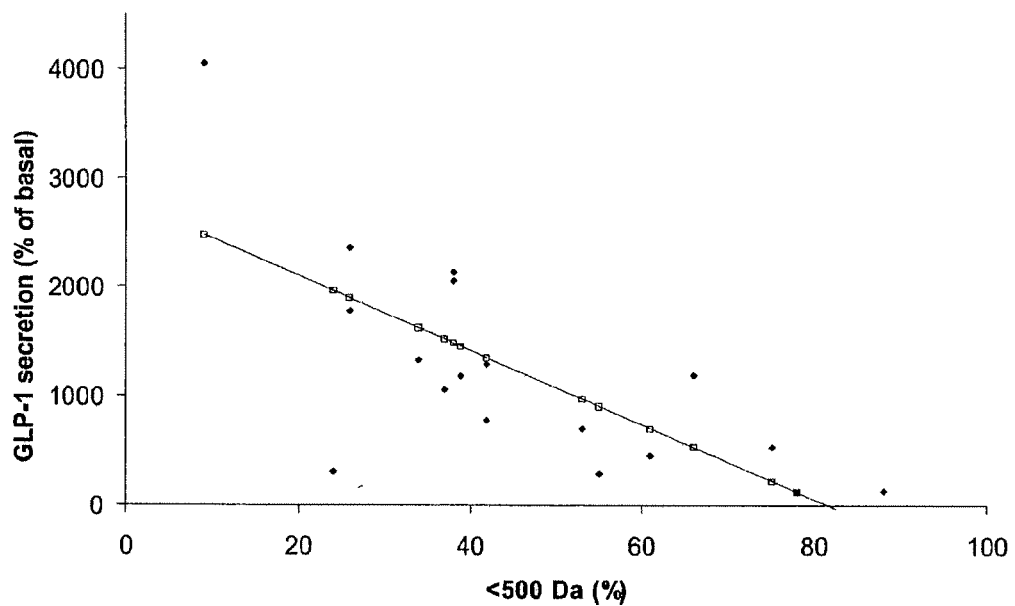
FIG. 1 shows GLP-1 activity expressed as a percentage of GLP-1 activity found in the absence of a hydrolysate.

The invention pertains to the use of protein hydrolysates for stimulating release of glucagon-like peptide 1 (GLP-1). GLP-1 is a 30 amino acid peptide having the amino acid sequence HAEGT FTSDV SSYLE GQAAK EFIAW LVKGR (SEQ ID NO: 1). In the present context, the term GLP-1 comprises analogues and homologues of GLP-1 which essentially retain the functionality of GLP-1, in particular its enhancing effect on glucose-dependent secretion of insulin by pancreatic β cells. In particular, extended and truncated forms are understood to be comprised by the term GLP-1, if they are capable of being induced by protein hydrolysates and are functionally equivalent to GLP-1. GLP-1 secretion can be detected by methods known in the art. The particular method used, such as immunoassay using specific antibodies, determines which analogues or homologues are detected.

It was found according to the invention that hydrolysates of natural proteins having a limited degree of hydrolysis are active in stimulating GLP-1 secretion in vitro. It was furthermore found that this direct stimulating effect is distinct from the indirect GLP-1-promoting effect of inhibiting its degradation by DPP-IV. Also, it was found that these effects can be added by providing hydrolysates of broad composition that have both a GLP-1 stimulating effect and a DPP-IV-inhibiting effect.

The protein hydrolysates to be used according to the invention can be obtained by chemical or enzymatic hydrolysis of natural proteins. The degree of overall hydrolysis if limited, ranging from as little as 1% (1 proteolytic cleavage on every 100 peptide bonds) up to about 40%. Preferably, the degree of hydrolysis is at least 2%, more preferably at least 4%, or even at least 8%, especially at least 10%, preferably up to 35%, most preferably up to 30%. The resulting hydrolysate to be used contains between 1 and 70 wt. % of peptides having a molecular weight of less than 500 Da, more preferably, between 5 and 60 wt. % or even from 8 up to 50 wt. %, especially from 12 up to 40 wt. % of such small peptides. The preferred weight proportion of peptides having a molecular weight of less than 1000 Da, is at least 5%, more preferably at least 15%, most preferably at least 35%, up to 85%, preferably up to 75%, more preferably below 65%. Independently, the preferred weight proportion of medium-sized peptides between 1000 and 5000 Da, is up from 12%, preferably at least 15%, especially at least 18% or even at least 24%, up to e.g. 80%, preferably 65%, in particular up to 50%. Alternatively or additionally, the hydrolysate to be used according to the invention can contain up to 55 wt % of peptides having a molecular weight between of 5000 Da and over, and preferably at least 1% or especially at least 3%, and no more than 45%, more preferably no more than 35%, and in particular up to 25 wt. %. These proportions are base on the total proteinaceous material of the composition.

The weight average molecular weight of the final hydrolysate to be used, optionally after fractionation or combination of different hydrolysates, is preferably between 500 and 8000 Da, more preferably between 800 and 5000 Da.

In a preferred embodiment, the hydrolysate also contains, or is even enriched compared to the starting protein, relative short peptides of from 2 up to 8 amino acids, preferably from 3 to 7 amino acids, preferably containing at least one proline residue. These peptides preferably comprise a proline residue as the first, second, third or fourth N-terminal residue, but mostly as second N-terminal residue. The proline is also found as C-terminal residue or penultimate C-terminal residue. The proline residue is mostly flanked by leucine, valine, or phenylalanine, but may also to a lesser extent be flanked by glutamine, alanine, histidine, isoleucine, glycine, methionine, and tyrosine. Most preferred are peptides having one of the N-terminal sequences LPX, VPX, XPL and XPV, wherein X is selected from L, V, I and F, and—slightly less preferred—A, G, H, M, Q and Y. Examples of suitable short peptides include LPL, IPI, PFP, LPLP (SEQ ID NO: 2), HPIK (SEQ ID NO: 3), LPVP (SEQ ID NO: 4), MPLW (SEQ ID NO: 5), GPFP (SEQ ID NO: 6), PLLQ (SEQ ID NO: 7), KVLP (SEQ ID NO: 8), APFPE (SEQ ID NO: 9), LPQYL (SEQ ID NO: 10), LPVPQ (SEQ ID NO: 11), VPYPQ (SEQ ID NO: 12), APFPEVF (SEQ ID NO: 13), GPFPIIV (SEQ ID NO: 14), EMPFPK (SEQ ID NO: 15), PQSVLS (SEQ ID NO: 16), YVPEPF (SEQ ID NO: 17), VPLGTQ (SEQ ID NO: 18), LPVPQK (SEQ ID NO: 19), LF, LL, II, LC and VTKCCTE (SEQ ID NO: 20). Thus, the composition may advantageously contain 5-60 wt. % of peptides having a molecular weight between 200 and 800 Da.

Although the inventors do not wish to be bound by any theory, it is contemplated that the larger peptides, having an average molecular weight above 500 Da, especially peptides having from 5 to 100 amino acids, more in particular from 8 to 50 amino acids, are active in inducing GLP-1 secretion, whereas the shorter peptides of 3-7 amino acids are active in inhibiting DPP-IV. Thus the combination of peptides has a beneficial double effect of increasing GLP-1 levels, which contributes to an optimum insulin release and glucose management.

As herein used, "protein hydrolysate" refers to a mixture of peptides derived from hydrolysis of one or more proteins with a certain degree of hydrolysis, i.e. the percentage of hydrolysed peptide bonds of the total amount of peptide bonds, of between 1% and 40%. The protein can be derived from one protein source or may be derived from more protein sources. Examples of such protein sources are micro-organisms (yeast, bacteria, fungi), plants (e.g. soy, pea, cotton, corn, wheat), animals, such as milk, blood, meat, egg and gelatine. Thus, the one or more proteins may be e.g. protein from micro-organisms, vegetable protein, animal protein, such as protein derived from meat scraps, fish, crustaceans or molluscs, milk protein and egg protein.

Hydrolysis of proteins can be performed by any means known in the art. Examples thereof include chemical hydrolysis and enzymatic hydrolysis. Examples of methods for chemical hydrolysis are well known in the art and comprise e.g. hydrolysis using cyanogen bromide, acid hydrolysis, e.g. using hydrochloric acid, or hydrolysis by means of fermentation of the one or more protein sources comprising the one or more proteins. Examples of methods for enzymatic hydrolysis are also well-known in the art and comprise hydrolysis using purified enzyme preparations or crude enzyme preparations. Enzyme preparations to be used may comprise endo- or exopeptidases, proteases, or mixtures thereof, and examples thereof include trypsin, chymotrypsins A, B and C, pepsin, rennin, microbial alkaline proteases, papain, ficin, bromelain, cathepsin B, collagenase, microbial neutral proteases, carboxypeptidases A, B and C, carnosinase, anserinase, V8 protease from *Staphylococcus aureus* and many more which are well-known to a person skilled in the art. Also combinations of these proteases may be used. Also commercially available enzyme preparations such as e.g. Alkalase, Chymotrypsine 800s, Neutrase, Flavourzyme (all available from Novo Nordisk, Denmark), Protex 6.0L, Peptidase FP (both available from Genencor, USA), Corolase L10 (Rohm, Germany), Pepsin (Merck, Germany), papain, pancreatin, proleather N and Protease N (Amano, Japan), or combinations thereof may be used. Enzymes prepared by means of recombinant DNA technology may also be used.

Combinations of enzymes, in particular combinations of one or more enzymes producing proline-containing peptides and one or more enzymes having another specificity, are well suited. The enzymes of a combination can be used simultaneously or consecutively.

It is preferred that the protein hydrolysates are obtained by enzymatic hydrolysis as discussed above, as enzymatic hydrolysis provides a suitable degree of hydrolysis and is conveniently performed. Moreover, the enzymes employed for enzymatic hydrolysis can be easily separated from the protein hydrolysate by means of simple column chromatography, such as e.g. gel filtration chromatography, or be inactivated by means of heat, acid, base, or the addition of inhibitors.

As an alternative, a combined hydrolysate may be used, in particular one hydrolysate (a) having a limited degree of hydrolysis of e.g. 1-30%, especially 2-20%, which is rich in peptides of between 5 and 50 amino acids, and another hydrolysate (b) having a higher degree of hydrolysis of e.g. 10-50%, especially 15-40%, which is rich in proline-containing peptides of 2-8 amino acids. The two (or more) hydrolysates may originate from one and the same protein, e.g. caseins or other milk proteins, or from different proteins, such as casein and whey or casein and a plant protein from e.g. wheat or soy. The weight ratio of the two hydrolysates may be between 1:9 and 9:1, especially between 1:3 and 3:1.

The protein hydrolysates may be fractionated by means of extraction, precipitation, filtration, ultrafiltration, nanofiltration, microfiltration or conventional column chromato-graphy (preferably ion exchange or affinity chromatography), or any combination of the above techniques, as to (further) concentrate the GLP-1 stimulating activity. As such, a fraction comprising a mixture of peptides or even single peptides may be identified that has an increased stimulating effect on GLP-1 compared to the starting protein hydrolysates. Such mixture of peptides or single peptides are also encompassed in the present invention. It is further envisioned that such peptides may be prepared by means of recombinant DNA technology, such as expression of the DNA encoding therefore in a suitable host, or by chemical synthesis.

The protein hydrolysate may be any protein hydrolysate, in particular a food protein hydrolysate, as such hydrolysate is considered food-grade and relatively easy to obtain. In a preferred embodiment of the present invention, the protein hydrolysate is a milk protein hydrolysate, such as a whey protein hydrolysate and more preferably a casein hydrolysate. The milk may originate from any mammal, especially from cattle, buffalo, sheep or goat, preferably from cattle (bovine milk). Alternatively, the hydrolysate may be e.g. an egg protein hydrolysate or a hydrolysate from plant proteins such as soy.

As used herein, a protein hydrolysate displays GLP-1 stimulating activity when in a GLP-1 assay as described in example 2, the concentration of GLP-1 is increased by a factor of at least 2, preferably at least 4, more preferably at least 10. A hydrolysate exhibits DPP-IV inhibiting activity when in the DPP-IV inhibition assay of example 3 an $IC_{50}$ (i.e. the concentration of inhibitor (in particular protein hydrolysate) that inhibits 50% of the DPP-IV activity) is displayed of at most 1000 µg/ml, preferably at most 800 µg/ml, more preferably at most 600 µg/ml, yet more preferably up to 400 µg/ml, and most preferably at most 300 µg/ml.

In a further aspect, the present invention relates to the use of a protein hydrolysate or a mixture according to the invention for the manufacture of a medicament, food supplement, beverage or food product for the prophylaxis and/or treatment of a GLP-1 mediated condition.

The term "prophylaxis" as herein used refers to preventing the emergence of a GLP-1 mediated condition in case no symptoms are as yet observed. As such, the protein hydrolysates may be employed to prevent deleterious GLP-1 mediated conditions from occurring, and may therefore be used to improve or stabilise health of any subject, in particular of a subject in need thereof.

As herein used, "a GLP-1 mediated condition" refers to any deleterious condition that arises or deteriorates which is due to the relative absence of GLP-1 or which can be improved by GLP-1. Examples of GLP-1 mediated conditions are disorders such as obesity, type 2 diabetes mellitus, and immunological disorders, such as autoimmune diseases, e.g. multiple sclerosis, rheumatoid arthritis, and Graves' disease. Other autoimmune diseases envisioned to benefit from stimulation of GLP-1 are type 1 diabetes mellitus, autoimmune haemolytic anaemia, Hashimoto's thyroiditis, myasthenia gravis, Goodpasture's syndrome, systemic lupus erythematosus, primary biliary cirrhosis, Sjögren's syndrome, chronic active hepatitis, mixed connective tissue disease, scleroderma, and chronic idiopathic thrombocytopenic purpura. Preferably the GLP-1 mediated condition is obesity and type 2 diabetes mellitus. The involvement of GLP-1 and DPP-IV in the pathogenesis of these disorders is well described in the literature and these disorders are therefore the major target of the hydrolysate or peptides according to the present invention.

In one embodiment, the protein hydrolysate or isolated peptide according to the present invention is used for the manufacture of a medicament, food supplement, beverage or food product for increasing satiety in a subject. As GLP-1 slows gastric emptying and inhibits food intake, a longer circulation half-life of GLP-1 as a result of enhanced secretion of GLP-1 or inhibition of the degradation enzyme DPP-IV will increase satiety in a subject, such that said subject will feel less hungry and have a reduced food intake. In particularly, subjects being overweight, such as e.g. obese subjects or subjects being only slightly overweight, will benefit from increased secretion of GLP-1 by administration of the protein hydrolysates according to the invention. The medicament, food supplement, beverage or food product can however also be employed to retain a certain weight so as to not get overweight, and may therefore be used to stabilise and/or improve the body weight for cosmetic purposes, i.e. for stabilising and/or improving appearance.

Therefore, in a further embodiment, the protein hydrolysate or isolated peptide according to the invention is used for the manufacture of a medicament, food supplement, beverage or food product for prophylaxis and/or treatment of obesity.

In another embodiment, the protein hydrolysate or isolated peptide according to the invention is used for the manufacture of a medicament, food supplement, beverage or food product for lowering of blood glucose levels. It has been found that blood glucose levels are reduced by ingestion of the hydrolysates, resulting in improved glucose management, which is particularly advantageous in diabetic subjects.

In a further embodiment, the protein hydrolysate or isolated peptide according to the invention is used for the manufacture of a medicament, food supplement, beverage or food product for increasing the pancreatic β-cell mass. It has been found that pancreatic β-cell mass increases by ingestion of the hydrolysate or peptides results in an improved insulin response and hence an improved glucose management, which is particularly advantageous in diabetic subjects.

In yet a further embodiment, the protein hydrolysate according to the invention is used for the manufacture of a medicament, food supplement, beverage or food product for prophylaxis and/or treatment of type 2 diabetes mellitus. Type 2 diabetes mellitus is characterised by resistance to insulin, such that the body does not respond to insulin appropriately, resulting in hyperglycaemia. It is often accompanied by obesity. As GLP-1 contributes to normalisation of blood glucose levels as well as to the control of satiety and obesity (body weight), increase of GLP-1 levels by increasing the circulation half-life thereof by administration of one or more protein hydrolysates according to the invention will contribute to the prophylaxis and treatment of type 2 diabetes mellitus, and/or will result in improved insulin sensitivity.

For use in a medicament or food supplement, the preparation can be combined with any suitable carrier, diluent, adjuvant, excipient etc., in order to obtain the medicament in the desired administration form. Advantageously, the medicament or food supplement is administered orally. The term "food supplement" is known in the art as any food component which provided specific nutritional or medicinal components and does not provide the full energy value required (i.e. generally less than 2000 or 2500 kcal/day) and includes food supplements in the form of a powder or medicament, as well as health products, such as health drinks. An ingredient that can be added to food before consumption or a preparation that can be consumed as such is also encompassed.

For the intended use, the protein hydrolysate according to the present invention may be administered alone or in admixture with a pharmaceutically acceptable carrier, in suitable pharmaceutical formulations which are a further object of the invention.

Examples of said formulations, which may be prepared using well known methods and excipients, such as those described in "Remington's Pharmaceutical Sciences Handbook", Mack Pub. Co., N.Y. U.S.A., are tablets, capsules, syrups, and the like for oral administration, whereas for the parental administration suitable forms are sterile solutions or suspensions in acceptable liquids, implants, etc.

The posology will depend on several factors such as type and seriousness of the pathological conditions to be treated, patient's weight and sex, etc. and will be easily determined by the skilled practitioner. Preferably, the hydrolysates of the invention are administered at a level of between 50 mg and 50 g, depending i.a. on the concentration of active peptides. Preferred dosage levels of the hydrolysates are between 200 mg and 20 g, more preferably between 500 mg and 5 g per day. As to active fractions, in particular the fraction having a molecular weight between 1000 and 5000 Da, the preferred level of administration is between 10 mg and 10 g of peptide mixture per individual per day, more preferred dosage levels for this fraction is between 40 mg and 2 g/day, and the fraction between 200 and 800 Da, is preferably administered at a level between 5 mg and 1 g peptides per day, preferably between 10 mg and 500 mg per day.

For use in a beverage or food product, the protein hydrolysate or isolated peptide or mixture thereof according to the present invention can be combined with any common food ingredient. The term "beverage" is meant to include cordials and syrups, as well as formulations of a dry powder to be dissolved in water or another liquid component for the preparation of instant drinks.

Preferably, the protein hydrolysate according to the present invention is administered in an amount of 0.001-0.5 g/kg body weight, depending type and seriousness of the pathological condition to be treated, weight and sex of the subject, etc. Such factors will easily be determined and taken into account by the skilled practitioner. Using such range, sufficient induction of GLP-1 and/or inhibition of DPP-IV will be achieved as to effect the desired level of activity of GLP-1 required for prophylaxis and/or treatment of the herein disclosed disorders and diseases.

The present invention is also directed to a method for prophylaxis and/or treatment of any GLP-1 mediated condition as discussed above, said method comprising administering an effective amount of the protein hydrolysate or the isolated peptide according to the present invention to a subject in need thereof.

The following examples are employed to further illustrate the present invention, but are in no way meant to limit the scope thereof.

Example 1

Preparation of Protein Hydrolysate for Improved GLP-1 Activity

One hundred gram of sodium caseinate was dissolved in 1800 g water with stirring. The pH was adjusted to pH 7.5. Water was then added to a final volume of 2000 ml. 25 milligrams of the protease trypsine dissolved in water was added and the mixture was incubated at 37° C. internal temperature for a 3 hours. The enzymatic reaction was then stopped by heating at 95° C. for 5 minutes. The mixture was then freeze-dried. The molecular weight distribution is given in table I (entry CAS002), and the GLP-1 stimulating and DPP-IV inhibiting activities were determined according to examples 2 and 3, respectively and are also given in table I.

Using other protein sources and varying enzymatic conditions, the hydrolysates mentioned in table I were obtained.

Example 2

In Vitro Measurement of GLP-1 Activity

The in vitro activity of GLP-1 was determined using the STC-1 cell line. STC-1 cells were cultured in flasks having a surface of 75 $cm^2$ and using DMEM medium supplemented with penicillin and streptomycin. For assays the cells were seeded in 96-wells microtiter plates and grown to a saturation density of 85%. Before each assay the cells were washed with HBSS buffer after which the hydrolysate dissolved in HBSS buffer was added to the cells. The plates were then incubated for 2 hours at 37° C. and 5% $CO_2$. 60 µl of the medium was taken and used for the GLP-1 ELISA (LINCO research) that determines the concentration of active GLP-1. The GLP-1 activities are expressed as percentage of the GLP-1 activity found in the absence of a hydrolysate (Table I; FIG. 1).

TABLE I

GLP-1 secretion and DPP-IV inhibition data of various hydrolysates

| Hydrolysate | DH (%) | Molecular weight distribution | | | | | | DPP-IV Inhibition (µg/ml) | GLP-1 secretion (%) |
| | | <500D (%) | 0.5 kD-1 kD (%) | 1 kD-2 kD (%) | 2 kD-5 kD (%) | 5 kD-10 kD (%) | >10 kD (%) | | |
| --- | --- | --- | --- | --- | --- | --- | --- | --- | --- |
| CAS001 | 6 | 9 | 8 | 9 | 18 | 17 | 37 | 3433 | 4045 |
| WGE001 | 10 | 24 | 20 | 17 | 20 | 9 | 6 | 1105 | 307 |
| CAS002 | 13 | 26 | 31 | 19 | 18 | 6 | 1 | 348 | 2362 |
| CAS003 | 17 | 26 | 30 | 26 | 20 | 4 | 1 | 739 | 1780 |
| WHE007 | 15 | 34 | 15 | 17 | 21 | 8 | 5 | 551 | 1330 |
| WHE003 | 20 | 37 | 16 | 14 | 5 | 13 | 0 | 645 | 1061 |
| WHE001 | 28 | 38 | 20 | 12 | 7 | 4 | 19 | 578 | 2130 |
| WHE006 | 17 | 39 | 21 | 18 | 4 | 1 | 0 | 516 | 1182 |
| EGG001 | 12 | 42 | 19 | 17 | 14 | 4 | 4 | 736 | 1285 |
| SOY002 | 26 | 42 | 21 | 13 | 7 | 2 | 3 | 980 | 778 |
| CAS004 | 20 | 53 | 28 | 15 | 4 | 0 | 0 | 536 | 702 |
| WHE005 | 29 | 55 | 31 | 11 | 3 | 0 | 0 | 723 | 282 |
| CAS005 | 27 | 61 | 21 | 13 | 5 | 0 | 0 | 726 | 452 |
| WHE002 | 40 | 66 | 18 | 8 | 7 | 0 | 0 | 346 | 1187 |
| SOY001 | 28 | 75 | 17 | 8 | 0 | 0 | 0 | 1239 | 530 |
| CAS006 | 39 | 78 | 16 | 5 | 1 | 0 | 0 | 292 | 121 |
| WHE004 | 67 | 88 | 10 | 2 | 0 | 0 | 0 | 747 | 131 |

Example 3

In Vitro Measurement of DPP-IV Activity

DPP-IV activity can be determined by measuring the increase in absorption at 385 nm using Gly-Pro-p-nitroanilide (Sigma G-0513) as DPP-IV substrate. A decrease in DPP-IV activity is a measure for the inhibition.

13.152 mg Gly-Pro-p-nitroanilide (substrate; Sigma G-0513) was dissolved in 1 ml Tris buffer, pH 8.0. DPP-IV (Sigma D-7052) was diluted with Tris buffer, pH 8.0 to 1.1 Unit/ml. The substrate was diluted 50-fold with Tris buffer, pH 8.0. The samples were prepared by diluting a protein hydrolysate to a 1 wt. % protein solution in Tris buffer, pH 8.0. The samples were then serially diluted to obtain a range of sample concentrations. 50 µl of the different serially diluted samples and 50 µl of the diluted substrate were then pipetted in wells of a microtiter plate with 96 wells. Subsequently, 100 µl of the diluted enzyme was pipetted in each well of a plate with 96 wells. Then the increase in absorption at 385 nm was determined and DPP-IV activities at different concentrations of a variety of protein hydrolysates were determined, from which the $IC_{50}$ (i.e. the concentration of inhibitor (particular protein hydrolysate) that inhibits 50% of the DPP-IV activity) could be derived. All hydrolysates had a degree of hydrolysis (DH) of more than 5%. As a control, two unhydrolysed proteins (Sodium caseinate from DMV International, NL, and Bipro from Davisco Foods, USA) with a degree of hydrolysis (DH) of 0% were tested. The degree of hydrolysis was determined using the o-phtaldialdehyde method, which is well known in the art. Thus, it was determined that many protein hydrolysates, in particular casein hydrolysates, had an $IC_{50}$ in the range of 290-1000 µg/ml, but that unhydrolysed protein did not inhibit the enzyme (Table I).

Example 4

In Vivo Study of Glucose Tolerance

Rats were offered a high-energy (4.4 kcal/g) diet (51.4 en % carbohydrate, 31.8 en % fat, 16.8 en % protein, #12266B Research Diets) and water ad libitum until after 19 weeks from birth. Then, the rats were introduced to a daily meal feeding regime in which the same food was freely available between 8 and 10 AM and between 2 and 4 µm. After 14 days, the rats were randomised in five groups (n=10) which were administered the following hydrolysates (Table I): CAS001, CAS002, CAS006 and WGE001. The hydrolysates were dissolved in milliQ water and administered as gavage approximately 4 ml per rat per gavage (4 ml/500 g bw), twice daily, 45 minutes before each meal (7:15 AM and 1:15 PM). Dosage of the hydrolysates was 800 mg per kg bw, and was continued for 5 weeks.

After 7 days of administration of the hydrolysates (=day 0) the acute glycemic capacity of the hydrolysates was evaluated by an acute oral glucose tolerance test (OGTT). Oral glucose (2 g/kg, glucose 500 mg/ml, Fresenius Kabi, SE) was given as gavage at 8:00 (=before the feeding period). Blood samples were taken from a tail vein and collected into heparinised tubes and EDTA tubes.

Figure 2:
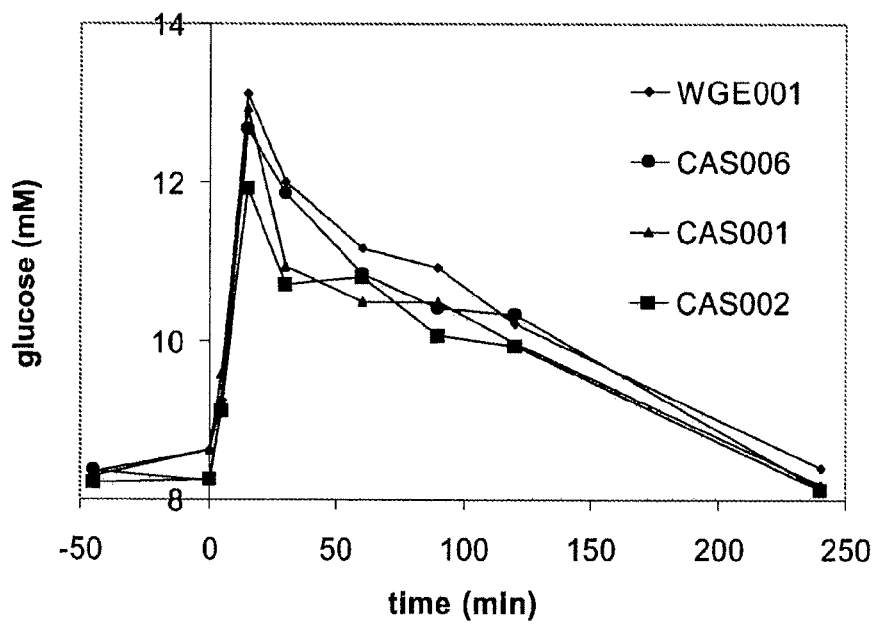
FIG. 2 shows plasma glucose levels after oral administration of glucose.
Figure 3:
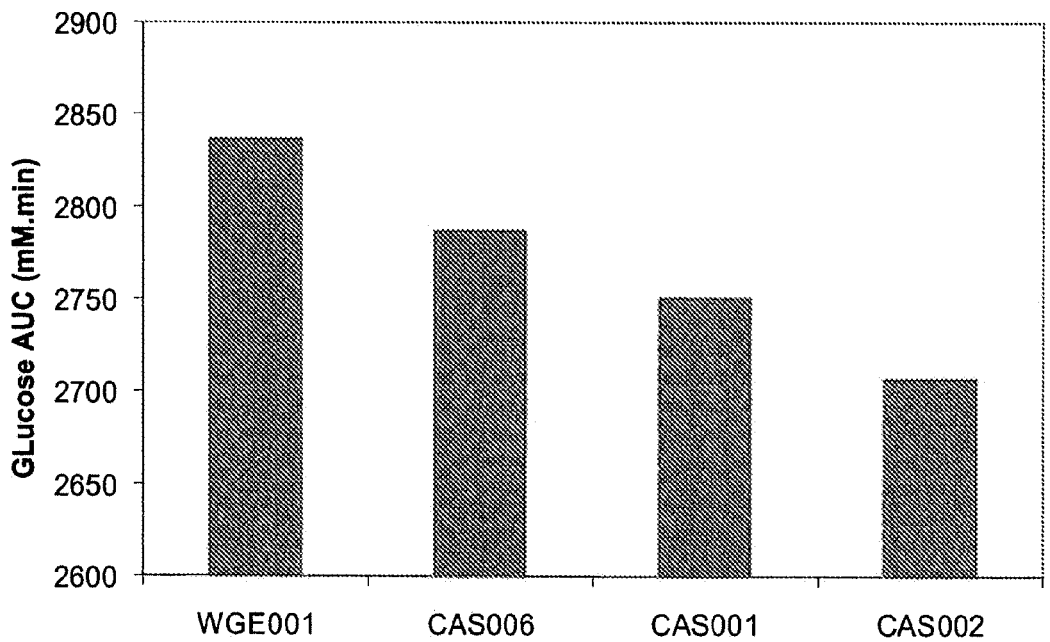
FIG. 3 depicts the integrated area under the curve of FIG. 2.

The heparinised blood samples were analysed on plasma glucose levels, using standard enzyme assay kits on an automated analyser (Vitross DTII). Plasma glucose levels were measured at −45, 0, 5, 15, 30, 60, 90, 120 and 240 minutes after the oral glucose (FIG. 2). FIG. 3 depicts the integrated area under the curve of FIG. 2.

Figure 4:
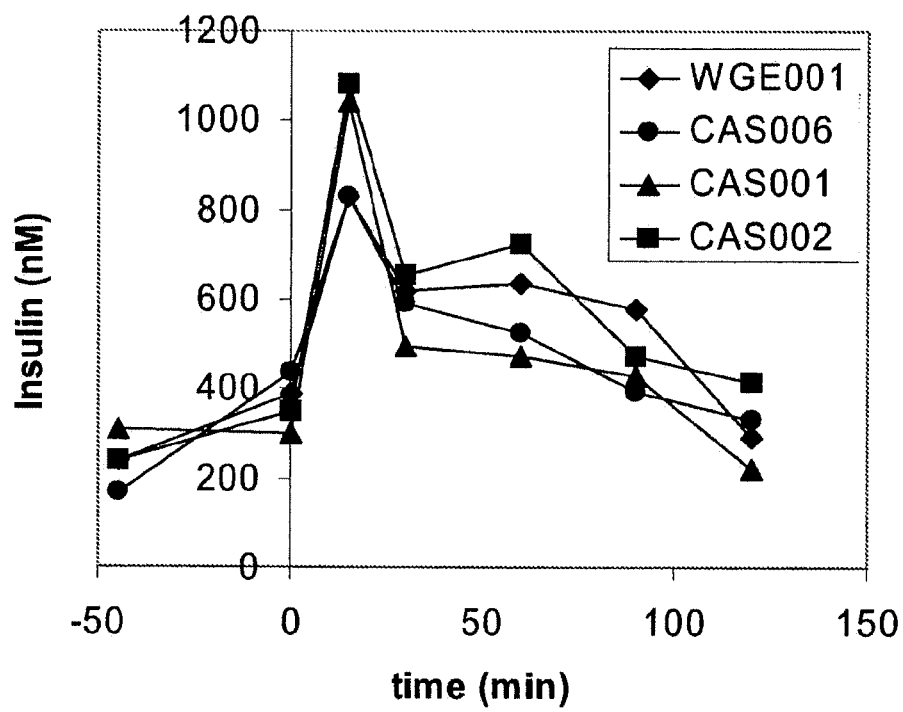
FIG. 4 shows plasma insulin levels after oral administration of glucose.

Plasma insulin was measured at −45, 0, 15, 30, 60, 90 and 120 minutes (FIG. 4). Plasma insulin was measured using dual samples for each data point using an ultra sensitive ELISA (Diamyd, SE).

Example 5

Preparation of Tablets Comprising the Hydrolysate or Peptide According to the Invention

| Tablet weight 633 mg. | |
|---|---|
| | Per 100 g |
| Hydrolysate CAS002 according to example I | 80.55 g |
| Microcrystalline cellulose[1] | 18.51 g |

| Tablet weight 633 mg. | |
|---|---|
| | Per 100 g |
| Magnesium Stearate | 0.47 g |
| Stearic Acid | 0.47 g |

[1]Avicel 102 - FMC

The powders were premixed whilst the Mg stearate was withheld for the last minutes of mixing. The stearates were mixed in at the end of the mixing process. The tablets were prepared by direct compression, and coated with Chr. Hansen Chroma tone DD8 8793-PK.

Tabletting parameters:

| | |
|---|---|
| Shape: | oblong |
| Weight | 633 mg |
| Length | 19 mm |
| Compression force | 13.3 kN |
| Hardness | 102 N |
| Disintegration time | 7 minutes. |

Example 6

Preparation of a Fermented Milk Drink Comprising the Product According to the Invention

| Ingredients: | Weight %. | |
|---|---|---|
| Skimmed milk | 80.2 | |
| Water | 11.4 | |
| Sugar | 8.0 | |
| Pectin | 0.3 | (Genupectin YM 115-L CP, Kelco) |
| Hydrolysate of example 1 | 0.95 | |
| Peach flavour | 0.06 | (B80631 TaKasago) |
| Colour | 0.013 | (Paprika 503160, Sensient food Colours) |
| Lactic acid | q.s. | |
| Culture | q.s. | (YC-X11, chr. Hansen) |
| Total | 100 | |

Method of Preparation:

Make a stock solution of pectin (4%) in a part of the water at 70° C. Mix the milk and the remaining water, and dissolve the product of the invention and the sugar in the milk. Pasteurise the solution at 90° C. for 5 minutes. Cool to fermentation temperature (42° C.), add the culture and ferment until the pH reaches 4.3. Add the pectin solution, while mixing vigorously. Then adjust the pH to 4.0 using lactic acid, homogenise the mixture at 120/120 bar at 40°, add the flavour and colour. Fill in cans and pasteurise at 80° C. for 3 minutes.

Example 7

Sugar-Free Drink Comprising the Product According to the Invention

| Ingredients: | Weight % | |
|---|---|---|
| Water | 96.0 | |
| Erythritol | 2.0 | Cargill Ceridex 16952 |
| Product of example 1 | 0.85 | |
| Citric acid | 0.35 | ADM |
| Sodium aspartate | 0.25 | Ajinomoto |
| Pectin | 0.1 | CP Kelco, YM100H |
| Orange flavour | 0.1 | Danisco #11009 |
| Pineapple flavour | 0.1 | Givaudan Roure #468529 |
| Mango flavour | 0.1 | Ottens #6252 |
| Sodium citrate | 0.08 | Staley FCC, USP dehydrate |
| Sucralose | 0.02 | McNeil Nutritionals |
| FD&C yellow #6 | 0.006 | |
| Total | 100 | |

Method of Preparation:

Dissolve the ingredients in water, but withhold the acid until last to adjust the pH to 3.85. Bottle the liquid and pasteurize for 1 minute at 85° C.

The invention claimed is:

1. A method for maintaining blood glucose homeostasis in a subject suffering from obesity or type 2 diabetes mellitus, comprising administering to a subject an effective amount of a proteinaceous material composition comprising a protein hydrolysate having a degree of hydrolysis between 1 and 40%, wherein the hydrolysate comprises:
   (a) between 12 and 80 weight percent of peptides having a molecular weight between 1000 and 5000 Da;
   (b) between 1 and 70 weight percent of peptides having a molecular weight of less than 500 Da;
   (c) less than 55 weight percent of peptides or proteins having a molecular weight of more than 5000 Da,
   the weight percentages being calculated on the basis of the total proteinaceous material of the composition,
wherein the hydrolysate comprises one or more peptides selected from the group consisting of LPL, IPI, PFP, LPLP (SEQ ID NO: 2), HPIK (SEQ ID NO: 3), LPVP (SEQ ID NO: 4), MPLW (SEQ ID NO: 5), GPFP (SEQ ID NO: 6), PLLQ (SEQ ID NO: 7), KVLP (SEQ ID NO: 8), APFPE (SEQ ID NO: 9), LPQYL (SEQ ID NO: 10), LPVPQ (SEQ ID NO: 11), VPYPQ (SEQ ID NO: 12), APFPEVF (SEQ ID NO: 13), GPFPIIV (SEQ ID NO: 14), EMPFPK (SEQ ID NO: 15), PQSVLS (SEQ ID NO: 16), YVPEPF (SEQ ID NO: 17), VPLGTQ (SEQ ID NO: 18), LPVPQK (SEQ ID NO: 19), LF, LL, II, LC and VTKCCTE (SEQ ID NO: 20), and
   wherein administration of the composition stimulates glucagon-like peptide-1 (GLP-I) secretion.

2. The method of claim 1, wherein the composition is administered at a level of between 100 mg and 50 g of protein hydrolysate per day.

3. The method according to claim 1, wherein the hydrosylate further comprises: (d) between 15 and 75 weight percent of peptides having a molecular weight of less than 1000 Da.

4. The method according to claim 3, wherein the hydrosylate comprises: (a) between 18 and 50 weight percent of peptides having a molecular weight between 1000 and 5000 Da; (b) between 8 and 50 weight percent of peptides having a molecular weight of less than 500 Da; (c) less than 45 weight percent of peptides or proteins having a molecular weight of more than 5000 Da; and (d) between 15 and 75 weight percent of peptides having a molecular weight of less than 1000 Da.

5. The method according to claim 3, wherein the hydrolysate comprises: (b) between 8 and 50 weight percent of peptides having a molecular weight of less than 500 Da; (c) up to 35 weight percent of peptides or proteins having a molecular weight of more than 5000 Da; and (d) between 15 and 65 weight percent of peptides having a molecular weight of less than 1000 Da.

6. The method according to claim 3, wherein the hydrolysate comprises: (a) between 24 and 50 weight percent of peptides having a molecular weight between 1000 and 5000 Da, and (c) up to 25 weight percent of peptides having a molecular weight above 5000 Da.

7. The method according to claim 1, wherein the protein hydrolysate comprises a milk protein hydrolysate.

8. The method according to claim 7, wherein the milk protein hydrosylate comprises a casein hydrolysate.

9. The method according to claim 1, wherein the hydrolysate comprises one or more peptides selected from LPL, LPLP (SEQ ID NO: 2), LPVP (SEQ ID NO: 4), MPLW (SEQ ID NO: 5), LPQYL (SEQ ID NO: 10), LPVPQ (SEQ ID NO: 11), VPYPQ (SEQ ID NO: 12), VPLGTQ (SEQ ID NO: 18), and LPVPQK (SEQ ID NO: 19).

10. The method according to claim 1, wherein the weight-average molecular weight of the hydrolysate is between 800 and 5000 Da.

11. A method of stimulating glucagon-like peptide-1 (GLP-1) secretion, comprising administering to a patient in need thereof an effective amount of a proteinaceous material composition comprising a protein hydrolysate having a degree of hydrolysis between 1 and 40%, wherein the hydrolysate comprises:
   (a) between 12 and 80 wt. % weight percent of peptides having a molecular weight between 1000 and 5000 Da;
   (b) between 1 and 70 wt. % weight percent of peptides having a molecular weight of less than 500 Da;
   (c) less than 55 wt. % weight percent of peptides or proteins having a molecular weight of more than 5000 Da,
   the weight percentages being calculated on the basis of the total proteinaceous material of the composition, and
wherein the hydrolysate comprises one or more peptides selected from the group consisting of LPL, IPI, PFP, LPLP (SEQ ID NO: 2), HPIK (SEQ ID NO: 3), LPVP (SEQ ID NO: 4), MPLW (SEQ ID NO: 5), GPFP (SEQ ID NO: 6), PLLQ (SEQ ID NO: 7), KVLP (SEQ ID NO: 8), APFPE (SEQ ID NO: 9), LPQYL (SEQ ID NO: 10), LPVPQ (SEQ ID NO: 11), VPYPQ (SEQ ID NO: 12), APFPEVF (SEQ ID NO: 13), GPFPIIV (SEQ ID NO: 14), EMPFPK (SEQ ID NO: 15), PQSVLS (SEQ ID NO: 16), YVPEPF (SEQ ID NO: 17), VPLGTQ (SEQ ID NO: 18), LPVPQK (SEQ ID NO: 19), LF, LL, II, LC and VTKCCTE (SEQ ID NO: 20).

12. The method according to claim 11, wherein the hydrosylate further comprises: (d) between 15 and 75 wt. % of peptides having a molecular weight of less than 1000 Da.

13. The method according to claim 12, wherein the hydrosylate comprises: (a) between 18 and 50 wt. % of peptides having a molecular weight between 1000 and 5000 Da; (b) between 8 and 50 wt. % of peptides having a molecular weight of less than 500 Da; (c) less than 45 wt. % of peptides or proteins having a molecular weight of more than 5000 Da; and (d) between 15 and 75 wt. % of peptides having a molecular weight of less than 1000 Da.

* * * * *

UNITED STATES PATENT AND TRADEMARK OFFICE
CERTIFICATE OF CORRECTION

PATENT NO. : 8,431,531 B2
APPLICATION NO. : 12/095346
DATED : April 30, 2013
INVENTOR(S) : Jan-Willem Pieter Boots Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 334 days.

Signed and Sealed this
Eighth Day of September, 2015

Michelle K. Lee
*Director of the United States Patent and Trademark Office*